United States Patent
Lu et al.

(10) Patent No.: US 6,621,192 B2
(45) Date of Patent: *Sep. 16, 2003

(54) INTEGRATED TUNABLE SURFACE ACOUSTIC WAVE TECHNOLOGY AND SENSORS PROVIDED THEREBY

(75) Inventors: Yicheng Lu, East Brunswick, NJ (US); Nuri W. Emanetoglu, Woodbury, NJ (US)

(73) Assignee: Rutgers, The State University of New Jersey, Piscataway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/905,205

(22) Filed: Jul. 13, 2001

(65) Prior Publication Data

US 2002/0043890 A1 Apr. 18, 2002

Related U.S. Application Data

(60) Provisional application No. 60/217,898, filed on Jul. 13, 2000, and provisional application No. 60/217,897, filed on Jul. 13, 2000.

(51) Int. Cl.$^7$ .............................................. H01L 41/08
(52) U.S. Cl. .............................. 310/313 A; 310/313 R; 310/313 D
(58) Field of Search ..................... 310/313 R, 313 D, 310/313 A

(56) References Cited

U.S. PATENT DOCUMENTS

| | | | |
|---|---|---|---|
| 4,345,176 A | * | 8/1982 | Grudkowski et al. ... 310/313 A |
| 4,900,969 A | * | 2/1990 | Mitsutsuka et al. ..... 310/313 A |
| 4,967,113 A | * | 10/1990 | Mitsutsuka ............. 310/313 A |
| 5,091,669 A | * | 2/1992 | Mitsutsuka ............. 310/313 A |
| 6,029,324 A | | 2/2000 | Wixforth |
| 6,194,808 B1 | * | 2/2001 | Yamanouchi et al. ... 310/313 D |
| 2002/0044028 A1 | * | 4/2002 | Lu et al. ................... 333/152 |

OTHER PUBLICATIONS

Rotter et al, "Quasi–monolithic GaAs/LiNbO/sub 3/–hybrids for acoustoelectric applications," Proceedings 1997 Ultrasonics Symposium, vol. 1, Aug. 1997, pp. 201–204.*
Rotter et al, "Voltage controlled SAW velocity in GaAs/LiNbO/sub 3/–hybrids," IEEE Transactions on Ultrasonics, Ferroelectric and Frequency Control, vol. 46 Issue 1, Jan. 1999, pp. 120–125.*
Rotter et al, "Significantly enchanced SAW transmission in voltage tunable GaAs/LiNbO/sub 3/ hybrid devices," Proceedings 1998 Ultrasonics Symposium, Jul. 1998, vol. 1, pp. 69–72.*

\* cited by examiner

*Primary Examiner*—Mark O. Budd
(74) *Attorney, Agent, or Firm*—Hoffmann & Baron, LLP

(57) ABSTRACT

The present invention provides a ZnO based tunable surface acoustic wave (SAW), preferably monolithically integrated tunable SAW (MITSAW) device. The MITSAW comprises a $ZnO/Mg_x Zn_{1-x}O$ quantum well structure and piezoelectric ZnO thin film epitaxially grown on R-plane sapphire $((01\bar{1}2)Al_2O_3)$ substrate using MOCVD. R-plane sapphire provides in-plane anisotropy in the ZnO layer as the c-axis of ZnO lies in the growth plane. A two-dimensional electron gas (2DEG) is placed in the delay path of the SAW device and interacts with the lateral electric field resulting in ohmic loss which attenuates and slows the surface acoustic wave. This mechanism is used to tune the acoustic velocity. The high coupling coefficients offered by the $ZnO/R-(Al_2O_3)$ system allows large velocity tuning. ZnO based MITSAW is used for chemical and biochemical sensors, offers excellent manufacturability, high yield and low cost. Such SAW sensors have a "resettable" sensing mechanism. The multiple acoustic wave modes are used for improved sensitivity and simultaneously use UV absorption measurement and SAW sensing mechanisms.

13 Claims, 3 Drawing Sheets

US 6,621,192 B2

INTEGRATED TUNABLE SURFACE ACOUSTIC WAVE TECHNOLOGY AND SENSORS PROVIDED THEREBY

CROSS-REFERENCE TO RELATED APPLICATIONS

This application claims priority to Provisional Application Ser. No. 60/217,898, filed on Jul. 13, 2000 and entitled "ZnO Based Tunable and Multi-mode Chemical and Biochemical SAW Sensor", and to Provisional Application Ser. No. 60/217,897, filed on Jul. 13, 2000 and entitled "ZnO Monolithically Integrated Tunable Surface Acoustic Wave Chip Technology".

FIELD OF THE INVENTION

This invention relates generally to tunable surface acoustic wave (SAW) technology and pertains more particularly to monolithically integrated tunable SAW (MITSAW) devices having a ZnO/Mg$_x$Zn$_{1-x}$O quantum well and sensors employing ZnO based MITSAW devices.

BACKGROUND OF THE INVENTION

Basic SAW Technology

SAW devices have been widely used for signal processing since 1964, when the interdigital transducer (IDT) was introduced. The basic principle of a SAW device is to apply an input IDT and an output IDT in mutually spaced relation to a piezoelectric member, to apply an electrical signal to the input IDT, thereby causing a surface acoustic wave to propagate in the piezoelectric member, and to obtain the electrical signal generated in the output IDT by the propagated surface acoustic wave. The time for the propagated wave to travel from its generation at the input IDT to its arrival at the output IDT constitutes a time delay and the piezoelectric member constitutes a delay path.

SAW Sensors

An important application of surface acoustic wave (SAW) devices is in the field of chemical and biochemical sensing. Surface acoustic waves are very sensitive to changes in the surface properties, including mass loading, conductivity, stress, or viscosity in liquid. Acoustic wave chemical and biochemical sensors have been popular and successfully used in military and commercial applications.

For chemical/biochemical sensing applications, the surface of the delay path (piezoelectric member) is coated with a chemically selective coating which bonds with the target chemical. This delay line is used in the feedback path of an oscillator circuit.

Known SAW sensors have several drawbacks. They are used in the "traditional" approach, where a single sensor is functionalized with a chemically sensitive material. While this approach is successful when there are a few chemicals present in the environment, its success depends on the availability of highly specific materials, such as suitable biological or molecular-recognition complexes. The mass-sensitive SAW devices can not differentiate between physisorbed and molecularly complexed mass on the surface of a device, unless a secondary perturbation such as a change in mechanical or electrical properties accompanies the mass change. SAW sensor arrays with different chemically independent selective coatings on each sensor have been used for sensing in environments containing many chemicals.

Tunable SAW Technology Using Quantum Well

SAW devices have been widely used for signal processing since 1964, when the interdigital transducer (IDT) was invented. The basic principle of the SAW devices is to use piezoelectric materials to convert an electrical signal into a mechanical wave in the launching transducer, and, conversely, to convert the mechanical wave into an electrical signal at the receiver transducer. An important parameter of a piezoelectric material is the electromechanical coupling coefficient, which is a measure of the conversion strength between electrical energy and mechanical energy. For SAW devices, the coupling coefficient is related to the difference of the metallized (i.e., short-circuited or infinite conductivity) and free surface (i.e., open circuit) velocities.

A problem in SAW technology to date has been the lack of tunability of acoustic velocity, which would allow tuning of the center frequency of the SAW filters. A conductive element near the piezoelectric surface changes the acoustic velocity by coupling with the electric fields of the acoustic wave. Ideally, tunability of the acoustic velocity is limited by the electromechanical coupling coefficient of the piezoelectric material. Early attempts include the use of a semiconductor film in close proximity to the piezoelectric surface. The variable finite conductivity of the semiconductor interacts with the electric fields associated with the acoustic wave, and slows the wave. An improved approach is to use a two dimension electron system (2DEG) to tune the acoustic velocity. An initial demonstration used GaAs/Al$_x$Ga$_{1-x}$As quantum well. As the piezoelectric coupling of GaAs is very small, the reported tunability range was <0.1%. An alternative hybrid GaAs —LiNbO$_3$ device where the 2DEG was formed in a GaAs quantum well, which was epitaxially lifted off, and bonded to the LiNbO$_3$ substrate. The effective coupling coefficient of this structure was reported to be 3.5% and a velocity tunability of 1.5% was reported. However, the epitaxial lift-off technology is very complicated, with low yields and poor reliability; therefore, it is unsuitable for commercial applications.

Zinc Oxide and its Related Compounds

Zinc oxide is a versatile semiconductor material, with a wide and direct energy band gap (approximately 3.3 eV at room temperature). It has an exciton binding energy (Eb) of 60 meV, which is 2.4 times the thermal energy at room temperature. The large Eb implies that electron-hole pairs are well bound even at room temperature, and efficient radiative recombination is possible if non-radiative recombination sites caused by crystal defects can be reduced by improving the quality of the film. Recently, ZnO has been used for visible-blind UV photodetectors. Optically pumped laser emission has been observed in ZnO films. This opens up the possibility of developing UV lasers from ZnO films. ZnO based ternary alloys, Mg$_x$Zn$_{1-x}$O, have been demonstrated, allowing the band gap to be extended up to 4.0 eV. In comparison with other wide band gap semiconductors, ZnO can be grown in the 300 degrees centigrade to 450 degrees centigrade range, hundreds of degrees lower than GaN.

ZnO films have recently been used as the substrate or buffer layer for the growth of GaN based optoelectronic devices. The lattice mismatch between GaN and ZnO is relatively small, which makes growth of high quality films possible. ZnO/GaN heterostructures have been used for hybrid optoelectronic devices. GaN films grown on high quality ZnO buffer layers (grown on C—(Al$_2$O$_3$)) have been observed to have better structural properties compared to GaN films grown on sapphire and SiC.

ZnO is well known as a piezoelectric material used in bulk acoustic wave (BAW) and surface acoustic wave (SAW) delay lines, filters and resonators in wireless communication and signal processing. ZnO thin films have been used in conjunction with low loss high acoustic velocity substrates, such as sapphire ($Al_2O_3$) and diamond; with semiconductors, such as Si, GaAs and InP; and with low coupling coefficient piezoelectric materials, such as quartz. ZnO thin films deposited on GaAs and on InP are also used for acousto-optic modulators.

MOCVD Technology

The key issue for high performance, thin film ZnO based SAW device fabrication is the control of the film quality. Many growth technologies have been used to grow ZnO films. Among them, MOCVD (metal organic chemical vapor deposition) technology offers the advantages of high quality epitaxial growth on large area substrates in a production scale.

Applicants herein have used an MOCVD system with a rotating disc reactor chamber. ZnO epitaxial films are grown, using DEZn as the zinc precursor and oxygen as the oxidizer. The gas phase reaction between DEZN and oxygen can occur at room temperature and results in particulate formation, which degrades ZnO film properties, including surface morphology and crystallinity. In order to minimize the gas phase reaction, the MOCVD reactor is designed to have a flow-top configuration with high nitrogen push flow. DEZn and oxygen are introduced into the reactor separately. The substrate is rotated at high speed for improving thickness uniformity.

SUMMARY OF THE INVENTION

The present invention has a primary object to provide a ZnO based tunable SAW, preferably monolothically integrated tunable SAW (MITSAW) technology.

More particularly, an object of the invention is to provide SAW sensors having a tunable feature, being able to operate in multiple acoustic wave modes and UV range, and having improved manufacturability.

In attaining these and other objects, the invention provides a SAW device built on piezoelectric ZnO film integrated with a ZnO and $Mg_xZn_{1-x}O$ quantum well structure.

In one form, the SAW device of the invention includes a piezoelectric member, input and output IDTs disposed on a surface of the piezoelectric member, and a quantum well structure engaged with the piezoelectric member.

The piezoelectric member is comprised of zinc oxide. The quantum well structure is composed of the binary semiconductor of zinc oxide and the ternary compound semiconductor of magnesium zinc oxide ($Mg_xZn_{1-x}O$). A substrate is provided for growth of the piezoelectric member and is comprised of R-plane sapphire.

The SAW device is built using R-plane sapphire substrate instead of the popular C-plane sapphire, which offers unique advantages; (i) the c-axis of the ZnO film in the ZnO/R—($Al_2O_3$) material system is in-plane, resulting with electrical, piezoelectric and optical anisotropy for novel applications; (ii) certain wave modes in the ZnO/R—($Al_2O_3$) material system have large coupling coefficients and low loss compared to the $GaAs/Al_xGa_{1-x}As$ material system, which significantly enhances the tunability of the acoustic velocity; and (iii) lattice mismatch between ZnO and R-plane sapphire is less than that between ZnO and C-plane sapphire, resulting in high quality ZnO thin films.

In another form, the tunable and multi-mode SAW sensors of the invention include a piezoelectric ZnO member, input and output IDTs disposed on a first surface of the piezoelectric ZnO member, and a quantum well structure disposed beneath a second surface of the piezoelectric ZnO member, the quantum well structure including a binary compound semiconductor of ZnO and a ternary compound of $Mg_xZn_{1-x}O$. The substrate is comprised of R-plane sapphire.

R-plane sapphire is chosen instead of the popular C-plane substrate, as this substrate provides in-plane anisotropy in the ZnO layer. Rayleigh waves, which are excited parallel to the C-axis, are used for gas-phase sensing, and Love waves, which are excited perpendicular to the C-axis, are used for liquid-phase sensing.

The high coupling coefficients offered by the ZnO/R-plane sapphire system allows velocity tuning larger than 1%. The sensor is "resetable" through this tuning mechanism, as operation of the sensor begins at the lower end of the velocity range. The velocity can then be returned to its original value by changing the 2DEG density through reducing the gate voltage. Multiple acoustic wave modes are induced in the layered structure in the high frequency ranges. The responses of the individual wave modes can be selected by adjusting matching networks at the input and output transducers (IDTs).

The sensor can also operate in a UV optical mode. Chemical and biochemical molecules have distinct signatures in the UV spectrum, allowing for accurate identification of the species absorbed by the sensitive coating. In the dual mode sensor operation, the sensor is used as an optical detector for identification of the absorbed species. The SAW response is used to monitor the absorption rate and amount.

In a further embodiment, the invention includes the above described sensor as one channel of a two channel sensor. The other channel includes structure which is identical to the one channel, except for the sensing coating. The two channels are placed in the feedback path of two identical oscillators, and the output of the circuit is the difference of the two frequencies. With this arrangement, the SAW sensor increases the sensing accuracy by eliminating response due to changes in the environment other than the monitored chemical species.

The foregoing and other objects and features of the invention will be further understood from the following detailed description of the preferred embodiments and practices and from the drawings.

DETAILED DESCRIPTION OF THE PREFERRED EMBODIMENTS AND PRACTICES

Figure 1:
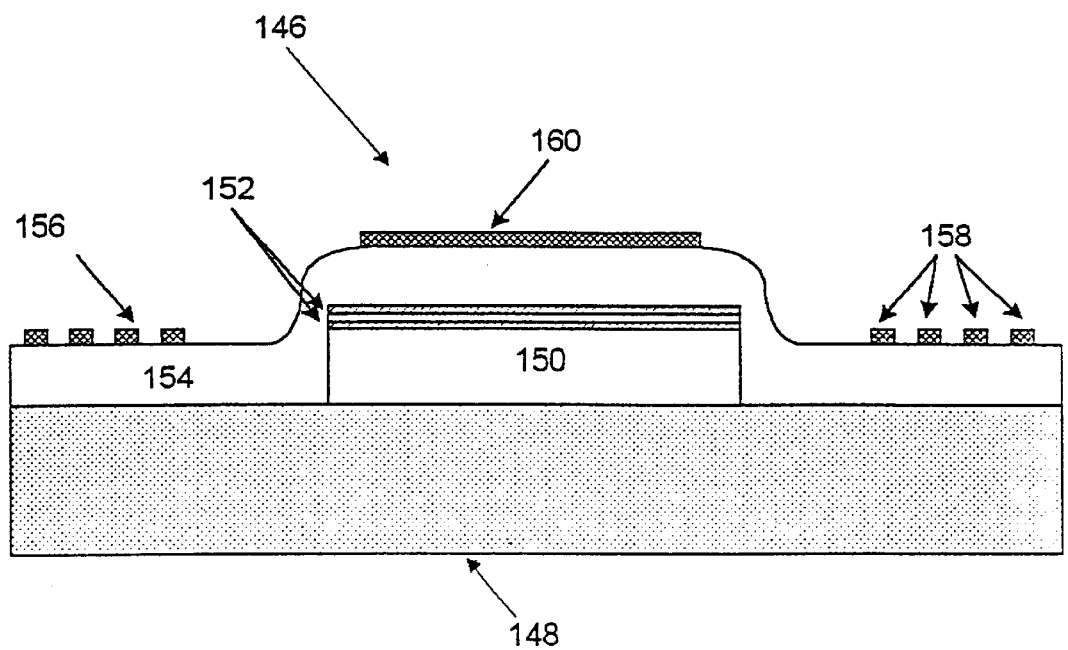
FIG. 1 is schematic showing of a ZnO monolithically integrated tunable SAW device of the invention.

Turning to FIG. 1, device 146 of the invention includes R-plane sapphire substrate 148, on which first ZnO layer 150 is centrally disposed. Quantum well structure 152 comprising the magnesium zinc oxide alloy is disposed atop layer 150. Second ZnO layer 154 is disposed both on substrate 148 and on quantum well structure 152. IDTs 156 and 158 are disposed on second ZnO layer 154 as is electrode 160.

ZnO layers 150 and 154 are compensatively doped to achieve piezoelectricity. The magnesium zinc oxide layer, which has x atoms of Mg and x-1 atoms of zinc oxide, is lightly doped to provide the electrons for the 2DEG. An important parameter for the magnesium zinc oxide layer is the ratio (x) of the Mg atoms in the ternary compound. This determines the band offset, which determines the threshold voltage of the 2DEG system, as well as the electron confinement in the quantum well.

Figure 2:
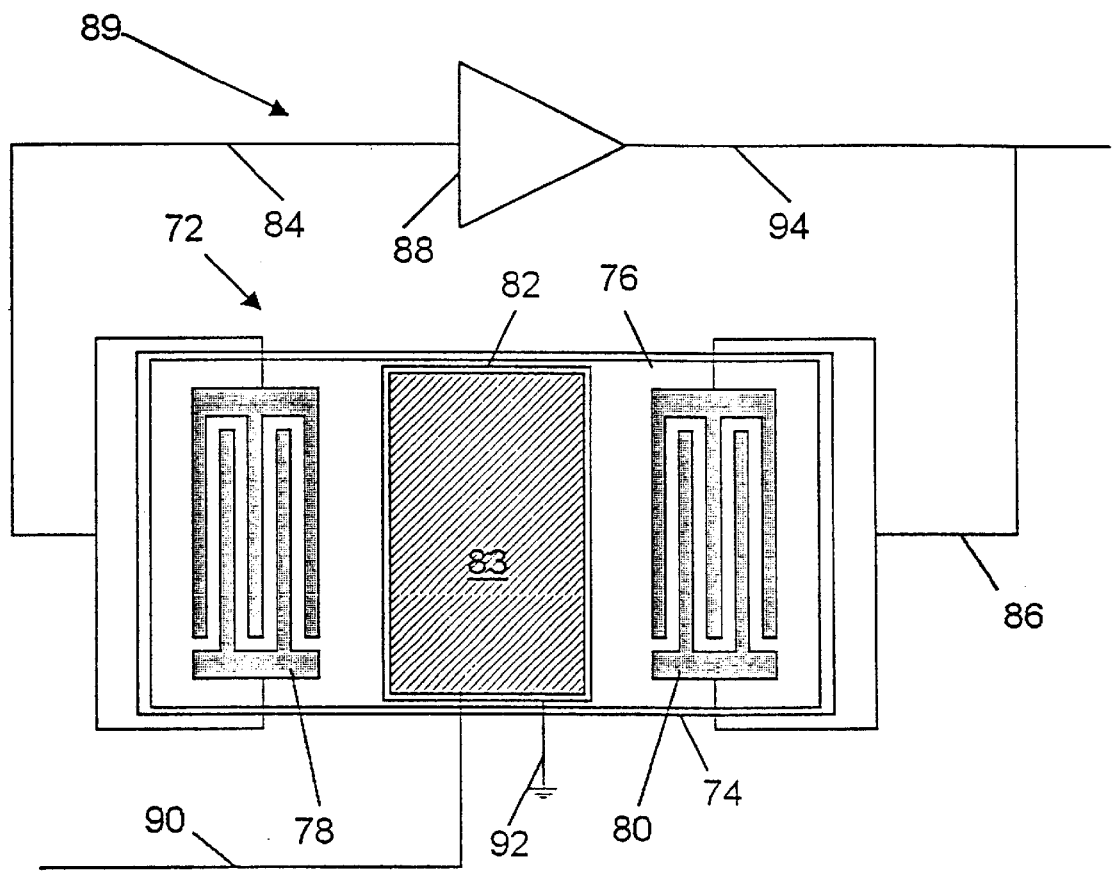
FIG. 2 is a schematic showing of a first embodiment of a ZnO MITSAW based single delay line oscillator sensor in accordance with the invention.

Referring to FIG. 2, device/sensor 72 includes a substrate 74, a piezoelectric member 76 disposed on substrate 74, IDTs 78 and 80, a quantum well structure 82 also disposed on substrate 74 and sensitive coating 83 disposed on ZnO/$Mg_xZn_{1-x}O$ quantum well structure 82. Device/sensor 72 is connected by conductors 84 and 86 in the feedback path of oscillator 88. Quantum well structure 82 has control electrodes (not shown) for applying bias thereto, the electrodes being connected to conductors 90 (gate or bias electrode) and 92, which is connected to electrical ground.

Substrate 74 is comprised of R-plane sapphire (R-$Al_2O_3$). Piezoelectric member 76 is W comprised of a layer of zinc oxide (ZnO). The R-plane sapphire substrate provides in-plane anisotropy in the zinc oxide layer. IDTs 78 and 80 are electrically conductive films deposited on piezoelectric member 76.

The oscillator output line 94 will exhibit frequency corresponding to the amount of delay in the feedback loop, which will in turn correspond to the target specimen sensed by device/sensor 72.

Quantum well structure 82, being placed in the delay path of device/sensor 72, interacts with the lateral electric field of the surface acoustic wave, resulting in ohmic loss, which attenuates and slows the wave. This mechanism is used to tune the acoustic velocity. The surface of the delay path, which is the gate area of the 2DEG, is coated with chemically selective sensing coating 83 which bonds with the target specimen.

Figure 3:
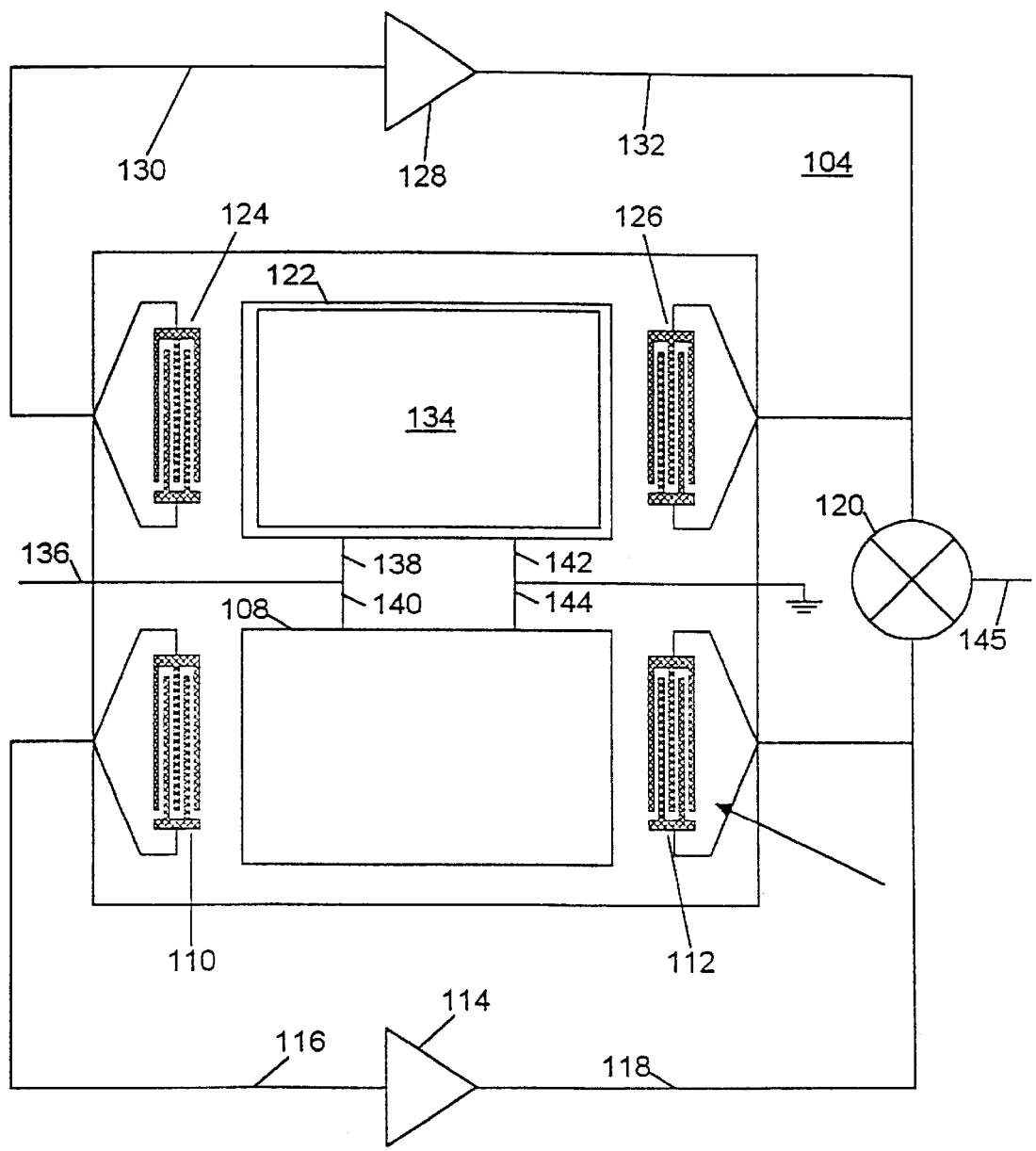
FIG. 3 is a schematic showing of a second embodiment of a ZnO based MITSAW based dual line oscillator (DDLO) sensor in accordance with the invention.

Turning to FIG. 3, a further sensor 104 in accordance with the invention is shown. Piezoelectric layer 106 is disposed atop a substrate (not shown) of R-sapphire. A lower channel disposed on layer 106 includes quantum well structure 108 and IDTs 110 and 112. The output of IDT 110 is applied to amplifier 114 over line 116 and the amplifier output is applied over line 118 to IDT 112 and to mixer 120. An upper channel disposed on layer 106 includes quantum well structure 122 and IDTs 124 and 126. The output of IDT 124 is applied to amplifier 128 over line 130 and the amplifier output is applied over line 132 to IDT 126 and to mixer 120.

The upper channel differs from the lower channel in including sensitive coating 134 on quantum well structure 122. The channels are otherwise identical and each quantum well structure receives the same bias from line 136 and lines 138 and 140, lines 142 and 144 being connected to electrical ground.

The output of mixer 120 on line 145 will provide indication of changes between the channel outputs, based on specimen collected on sensitive coating 134.

As above noted, the two channels are placed in the feedback path of two identical oscillators, and the output of the circuit is the difference of the two frequencies. Sensing accuracy is increased by eliminating response due to changes in the environment other than the monitored chemical series.

Various changes may be introduced in the disclosed preferred embodiments and practices without departing from the invention. Accordingly, it is to be appreciated that the true spirit and scope of the invention is set forth in the following claims.

What is claimed is:

1. An integrated multi-mode tunable SAW device comprising a piezoelectric member comprised of zinc oxide, a quantum well structure comprised of the zinc oxide and magnesium zinc oxide heterostructure, disposed on a first layer of said piezoelectric member, input and output IDTs disposed on a second layer of said piezoelectric member, a metal electrode disposed on said heterostructure and on said piezoelectric member, and a R-plane sapphire substrate on which said first and second layers of said piezoelectric member are disposed.

2. The integrated multi-mode tunable SAW device claimed in claim 1, wherein said electrode is a patterned metal layer controlling electron conductivity in said quantum well structure.

3. The integrated multi-mode tunable SAW device claimed in claim 1, wherein said R-plane sapphire substrate provides in-plane anisotropy in said piezoelectric member.

4. The integrated multi-mode tunable SAW device claimed in claim 1, wherein said quantum well structure comprises ZnO/$Mg_xZn_{1-x}O$ monolithically integrated on said R-plane sapphire substrate through a crystal growth technique.

5. The integrated multi-mode tunable SAW device claimed in claim 4, wherein said crystal growth technique is MOCVD.

6. The integrated multi-mode tunable SAW device claimed in claim 1, wherein said second layer of said piezoelectric member is disposed on said quantum well structure.

7. The integrated multi-mode tunable SAW device claimed in claim 1, wherein said electrode is disposed on a SAW path of said second layer of said piezoelectric member.

8. The integrated multi-mode tunable SAW device claimed in claim 1, wherein said R-plane sapphire substrate provides high acoustic velocity in said piezoelectric member.

9. The integrated multi-mode tunable SAW device claimed in claim 1, wherein said R-plane sapphire substrate provides low lattice mismatch in said piezoelectric member.

10. The integrated multi-mode tunable SAW device claimed in claim 3 wherein waves generated in said piezoelectric member are capable of being used for gas-phase and liquid-phase sensing.

11. The integrated multi-mode tunable SAW device claimed in claim 10, wherein said waves are Rayleigh waves excited parallel to a c-axis of the zinc oxide and is used for said gas-phase sensing.

12. The integrated multi-mode tunable SAW device claimed in claim 10, wherein said waves are Love waves excited parallel to the c-axis of the zinc oxide and is used for said liquid-phase sensing.

13. The integrated multi-mode tunable SAW device claimed in claim 1, wherein said device can be simultaneously operated for SAW and UV optical sensing.

* * * * *